(12) United States Patent
Ikebukuro

(10) Patent No.: US 8,981,075 B2
(45) Date of Patent: Mar. 17, 2015

(54) PSA BINDING APTAMER AND METHOD FOR DIAGNOSIS OF PROSTATE CANCER

(75) Inventor: Kazunori Ikebukuro, Tokyo (JP)

(73) Assignee: National University Corporation Tokyo University of Agriculture and Technology, Tokyo (JP)

( * ) Notice: Subject to any disclaimer, the term of this patent is extended or adjusted under 35 U.S.C. 154(b) by 208 days.

(21) Appl. No.: 13/806,998

(22) PCT Filed: Jul. 2, 2010

(86) PCT No.: PCT/JP2010/061652
§ 371 (c)(1),
(2), (4) Date: Sep. 23, 2013

(87) PCT Pub. No.: WO2012/001820
PCT Pub. Date: Jan. 5, 2012

(65) Prior Publication Data
US 2014/0011207 A1    Jan. 9, 2014

(51) Int. Cl.
*C07H 21/04*       (2006.01)
*C12N 15/115*     (2010.01)
*G01N 33/574*    (2006.01)

(52) U.S. Cl.
CPC ........ *C12N 15/115* (2013.01); *G01N 33/57434* (2013.01); *G01N 33/57488* (2013.01); *C12N 2310/16* (2013.01)
USPC ...................................................... 536/24.5

(58) Field of Classification Search
USPC ...................................................... 536/24.5
See application file for complete search history.

(56) References Cited

FOREIGN PATENT DOCUMENTS

| JP | 2006-042645 A | 2/2006 |
|---|---|---|
| JP | 2007-014292 A | 1/2007 |
| JP | 2009-183192 A | 8/2009 |
| WO | WO 2006/096754 A2 | 9/2006 |
| WO | 2009/003145 A1 | 12/2008 |
| WO | 2009/053691 A1 | 4/2009 |

OTHER PUBLICATIONS

Supplementary European Search Report dated Nov. 11, 2013 in European Application No. 10854117.8, 10 pages.
Jeong et al., "Slection of RNA Aptamers Specific to Active Prostate-Specific Antigen," *Biotechnol. Lett.* (2010) 32:379-385.
Chinese Office Action for Chinese Application No. 201080067716.3 dated Dec. 12, 2013.
Ikebukuro et al.; "A novel method of screening thrombin-inhibiting DNA aptamers using an evolution-mimicking algorithm"; *Nucl. Acids Res.;* 33(12):e108 (7 pages (2005)) published online Jul. 7, 2005.
Ikebukuro et al.; "Analysis of thrombin-inhibiting DNA aptamers using a genetic algorithm"; *Biotechnol. Lett.;* 28(23):1933-1937 (2006).
Ikebukuro et al.; "Selection of DNA aptamer against prostate specific antigen"; *National Meeting of the Chemical Society of Japan;* 90(3):783 Abstract 3D4-31 (Mar. 2010) (2 pages).
Jeong et al.; "Selection of RNA aptamers specific to active prostate-specific antigen"; *Biotechnol. Lett.;* 32(3):379-385 (Mar. 2010).
International Search Report from PCT/JP2010/061652, dated Aug. 17, 2010 (5 pages).
News Letter, Division of Biological Function-related chemistry, The Chemical Society of Japan, Mar. 9, 2010, vol. 24, No. 4, p. 20.
Office Action for Japanese Application No. 2012-557352 dated Oct. 28, 2014, 12 pages, with English translation.

*Primary Examiner* — Brian Whiteman
(74) *Attorney, Agent, or Firm* — Kilpatrick Townsend & Stockton LLP

(57) ABSTRACT

The present invention provides an aptamer that binds to prostate-specific antigen (PSA), the aptamer including: a preceding region having a random polynucleotide sequence consisting of from 1 to 10 nucleotides; a first region, at a 3' end of the preceding region, consisting of nnnnCT wherein each n is independently selected from A, T, G and C; a second region consisting of nnCTTT wherein each n is independently selected from A, T, G and C, and at least one part of the second region is complementary to the first region; and a third region positioned between the first region and the second region and consisting of a random polynucleotide sequence having from 3 to 30 nucleotides.

10 Claims, 6 Drawing Sheets

PSA BINDING APTAMER AND METHOD FOR DIAGNOSIS OF PROSTATE CANCER

TECHNICAL FIELD

This application is the U.S. National Phase entry under 35 U.S.C. §371 and claims the benefit of International Application No. PCT/JP2010/061652, filed Jul. 2, 2010, all of which is incorporated herein by reference in its entirety for all purposes.

REFERENCE TO SEQUENCE LISTING SUBMITTED AS TEXT FILE

This application includes a Sequence Listing as a text file named "34696_000400US_860873_SEQ_TXT.txt" created Dec. 26, 2012, and containing 8,405 bytes. The material contained in this text file is incorporated by reference in its entirety for all purposes.

BACKGROUND ART

Prostate-specific antigen (PSA) is a 33 to 34 kDa glycoprotein produced primarily by prostate epithelium, and is known as the most common serum marker for diagnosing prostate cancer. Prostate cancer usually leads to the release of high concentrations of PSA into the circulatory system and causes serum PSA levels to rise up to $10^5$-fold. Thus, measurement of serum PSA is widely used for early detection and monitoring of patients with prostate cancer. A serum PSA measurement above a cut-off value of 4.0 ng/mL is generally regarded as positive and might indicate the need for a biopsy.

Aptamers are nucleic acid ligands that can recognize various target molecules, such as proteins and small molecules, with high affinity and specificity comparable to those of monoclonal antibodies. Aptamers, especially DNA aptamers, are easily and inexpensively synthesized and chemically modified. Furthermore, they can be designed to undergo structural changes when they bind to targets. These features make DNA aptamers ideal for molecular recognition elements in biosensors. Using the advantages of aptamers, aptamer-based highly sensitive detection systems have been constructed.

Target-binding ability is the most important feature in terms of applying an aptamer to a biosensor. Aptamers are generally selected from random sequence pools in vitro using a process referred to as SELEX (systematic evolution of ligands by exponential enrichment) based on target-binding activity. SELEX is an efficient screening method because iterative cycles of selection can be carried out using Polymerase Chain Reaction (PCR).

Under these circumstances, various aptamers are known as detection tools for, for example, prion specific proteins (JP No. 2006-42645 A 1), vascular endothelial growth factors (JP 2008-237042) and insulin (JP No, 2009-183192 A1).

In particular, WO2006/096754 describes stabilized aptamers capable of binding to prostate-specific membrane antigen (PSMA) and their use as prostate cancer therapeutics, and discloses that aptamers obtained by minimization and optimization have Kd (dissociation constant)=2 to 10 (nM).

On the other hand, it is known that SELEX sometimes fails to screen for aptamers with high affinity to target molecules and that the actual size and complexity of the sequence space in which aptamers are screened by SELEX is smaller than expected. In order to obtain an aptamer having higher affinity, various modification methods of screening by SELEX are known, such as a selection method for DNA aptamer using genetic algorithms (GAs) (see, for example, Nucleic Acids Res., 2005, Vol. 33 (12), e108, JP No. 2007-14292 A). For the selection of aptamer using GA based on target-binding ability, candidate oligonucleotides are first pre-selected by SELEX. Their oligonucleotide sequences are then amplified, crossed over and mutated in silico using GA. After the GA operations are performed, a new set of sequences is synthesized and assayed in vitro. Then, sequences with high binding ability are selected for a next cycle of GA. By repeating the process of GA operation, the sequence space, which cannot be fully screened only by SELEX, can be covered.

However, because the binding ability of an aptamer is generally lower than that of an antibody, aptamers are not generally practical as diagnosis tools, and, for example, the PSMA binding aptamers described above are not sufficient for diagnosis of prostate cancer for the same reason.

DISCLOSURE OF INVENTION

The present invention has been made in view of the above circumstances and provides an aptamer, a method for diagnosis of prostate cancer and a method for preparing an aptamer.

A first aspect of the invention provides an aptamer that binds to prostate-specific antigen (PSA), the aptamer including: a preceding region having a random polynucleotide sequence consisting of from 1 to 10 nucleotides; a first region, at a 3' end of the preceding region, consisting of nnnnCT wherein each n is independently selected from A, T, G and C; a second region consisting of nnCTTT wherein each n is independently selected from A, T, G and C, and at least one part of the second region is complementary to the first region; and a third region positioned between the first region and the second region and consisting of a random polynucleotide sequence having from 3 to 30 nucleotides A second aspect of the invention provides a method for diagnosis of prostate cancer, comprising contacting the aptamer described above with a body fluid sample from a subject.

In some embodiments, the aptamer (SEQ ID NO: 1) described above is one of:

(1) polynucleotides of SEQ ID Nos. 1 to 7;

(2) polynucleotides having the same sequence as SEQ ID Nos. 1 to 7, except that from one to 5 nucleotides are different in each of the third region and the preceding region, respectively; or (3) polynucleotides having the same sequence as SEQ ID Nos. 1 to 7, except that a total of from one to 5 nucleotides are different in the first region and the second region thereof, and from one to 5 nucleotides are different in each of the third region and the preceding region, respectively.

DESCRIPTION OF PREFERRED EMBODIMENT

The aptamer according to the invention is an aptamer that binds to prostate-specific antigen (PSA), the aptamer including: a preceding region having a random polynucleotide sequence consisting of from 1 to 10 nucleotides; a first region, at a 3' end of the preceding region, consisting of nnnnCT wherein each n is independently selected from A, T, G and C; a second region consisting of nnCTTT wherein each n is independently selected from A, T, G and C, and at least one part of the second region is complementary to the first region; and a third region positioned between the first region and the second region and consisting of a random polynucleotide sequence having from 3 to 30 nucleotides According to the present invention, since the aptamer of the invention has a first region, at a 3' end of the preceding region, consisting of a specific sequence and a second region consisting of a specific sequence connected via a third region consisting of a random polynucleotide sequence, the aptamer has the specific secondary structure and higher affinity to PSA than other aptamers that bind to PSA, and the binding ability of the aptamer according to the invention is almost equal to that of antibodies.

In the invention, the term "step" as related to a method indicates not only an independent step but may also indicate a step which cannot be discriminated clearly from other steps, as long as the intended effects of the step may be obtained.

Further, any notation for expressing numerical ranges in the invention indicates a range defined by the minimum and maximum values and includes the minimum and maximum values.

Unless otherwise indicated, the content amount of respective components in compositions in the present invention refer to the amount of one component when one of the components corresponding to the respective components defined in the present invention is included in a composition, and to the total amount when two or more components are included.

The invention will be described below.

As described above, the aptamer of the invention consists of the preceding region; the first region; the second region; and the third region, and has a stem part (a double strand region) formed by the first region and the second region, and loop parts (single strand regions) formed by the preceding region and the third region, respectively, such that the secondary structure of the aptamer of the invention is a hair-pin structure.

The term "a stem part" in the specification means a region that two polynucleotides may form an overall double strand region in accordance with their complementarity. Thus, the term may not only include a case where the region consists of two polynucleotide sequences that are completely complementary but also a case where the region consists of two polynucleotide sequences that are not completely complementary as long as at least one part of the polynucleotides are complementary and an overall double strand region may be formed.

Figure 1:
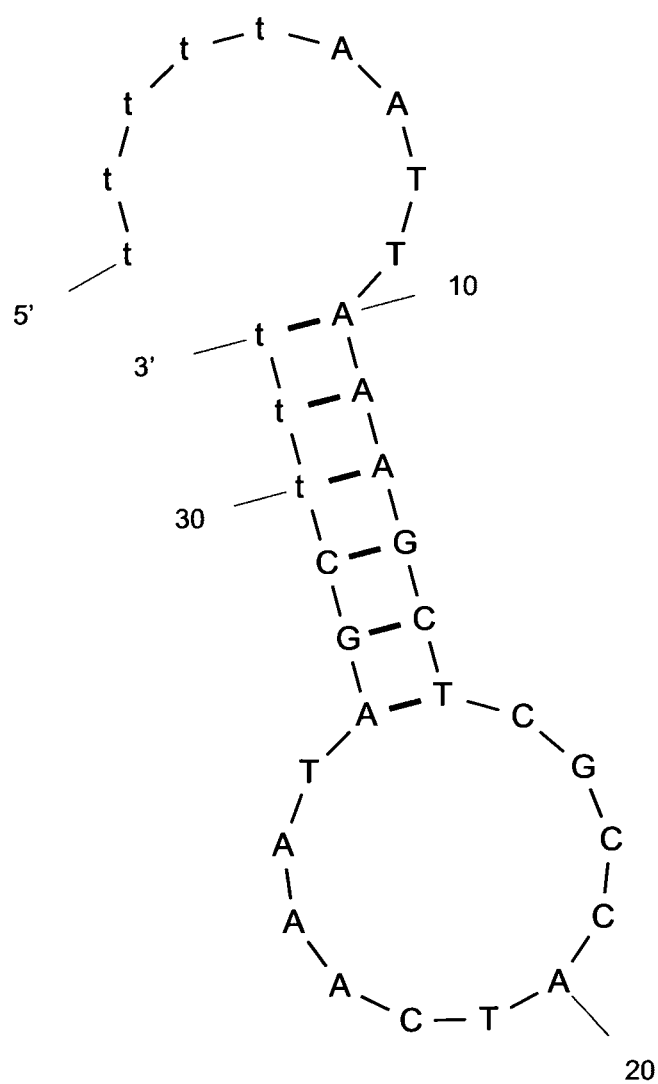
FIG. 1 is a diagram showing a predicted secondary structure of the aptamer of the invention.

The sequence of the second region may be selected so as to be able to form the double strand region—that is, the stem part—and at least one part of the second region consists of a nucleotide that is complementary to the first region. The third region consists of a random polynucleotide sequence having from 3 to 30 nucleotides and forms a single strand loop. While the specific reason for this remains unexplained, it is thought that the high affinity to PSA of the aptamer of the present invention is attributable to this structure. (See FIG. 1.)

The first region is positioned at a 3' end of preceding region and forms the double strand region with the second region. In view of the binding affinity to PSA, the first region is preferably (A or C)A(A or G)GCT, and, more preferably, the first region is AAAGCT, AAGGCT or CAGGCT.

In view of the binding affinity to PSA, the second region is preferably (A or C,)(A or G)CTTT and, even more preferably, the second region is A(A or G)CTTT, further more preferably, AGCTTT or AACTTT.

The preceding region of the aptamer has a random polynucleotide sequence consisting of from 1 to 10 nucleotides in order to stabilize the secondary structure of the aptamer. In view of the binding affinity to PSA, the preceding region preferably consists of $T_m$ (A or T)(A or C)T(T or G), and m is an integer of 1 to 10, preferably 1 to 5. The more preferably preceding region may have TTTTTAATT or TTTTTAATG or a polynucleotide sequence having from 1 or 2 bases that are different therefrom, such that TTTTTTATT, TTTTTACTG, or the like.

The third region has from 3 to 30 random polynucleotide sequences and forms a loop portion. In view of the stability of the loop, the random polynucleotide sequence includes preferably 3 to 20 nucleotides, more preferably 5 to 15 nucleotides, and yet more preferably 7 to 13 nucleotides. The kind of nucleotide composing of the random polynucleotide sequence is not limited and the one skilled in the art may produce the random polynucleotide sequence for the third region. In view of the binding affinity to PSA, the third region may most preferably be CGCCATCAAAT (SEQ ID No. 12) or a polynucleotide sequence having from 1 to 5 bases that are different therefrom, such as CGCCATCAGAT (SEQ ID No. 13), CGCCATCAAAG (SEQ ID No. 14), or the like.

In particular, the aptamer binding to PSA of the present invention is preferably one of the following:

(1) polynucleotides of SEQ ID Nos. 1 to 7, (2) polynucleotides having the same sequence as SEQ ID Nos. 1 to 7, except that from one to 5 nucleotides are different in each of the third region and the preceding region, respectively, or, (3) polynucleotides having the same sequence as SEQ ID Nos. 1 to 7, except that a total of from one to 5 nucleotides are different in the first region and the second region thereof, and from one to 5 nucleotides are different in the third region and the preceding region, respectively.

The polynucleotides described in (3) above differ from the SEQ ID Nos. 1 to 7 by from 1 to 15 nucleotides, since polynucleotides having differences in this range may have a similar binding ability to PSA. The preferable polynucleotides described in (3) or (2) above are selected from combinations of the preferable polynucleotides described above for the first region, the second region, the third region and the preceding region.

Since the aptamer of the present invention may be produced using an automated chemical synthesizer, they can be prepared much more easily and inexpensively than specific antibodies.

TABLE 1

| NAME | SEQUENCE | SEQ. ID NO. |
|---|---|---|
| APSap4#5 | TTTTTAATTAAAGCTCGCCATCAAATAGCTTT | 1 |
| APSap3'#04 | TTTTTAATTAAGGCTCGCCATCAAATAGCTTT | 2 |
| APSap4#10 | TTTTTTATTAAGGCTCGCCATCAAATAGCTTT | 3 |
| APSap4#7 | TTTTTAATTAAGGCTCGCCATCAGATAGCTTT | 4 |
| APSap4#14 | TTTTTAATTAAGGCTCGCCATCAAAGAGCTTT | 5 |
| APSap4#11 | TTTTTAATTAAGGCTCGCCATCAAATAACTTT | 6 |
| APSap4#1 | TTTTTAATTCAGGCTCGCCATCAAATAGCTTT | 7 |
| APSap2#02 | TTTTTAATTAAGGATTTCCCGGTTGTATCTTT | 8 |
| APSap2#18 | TTTTTAATGTCAACGTTGTTTACTGTCCCTTT | 9 |
| APSap2#16 | TTTTTACTGTGAACTCGCCATCAAATATCTTT | 10 |

Although aptamers that bind to PSA, including the aptamers described above, may be obtained by a known SELEX method, a modified SELEX method may preferably be used. A preferable method of preparing aptamer that binds to PSA may be a method including:

performing SELEX selection treatment using PSA immobilized on a solid phase to obtain candidate sequences consisting of single strand polynucleotides;

modifying the candidate sequences by performing crossover between different candidate sequences and point random mutation for each of the candidate sequences to obtain modified candidate sequences; and sorting modified candidate sequences based on PSA binding ability to obtain the aptamer.

SELEX selection in the method for preparing an aptamer is known to those skilled in the art and the SELEX selection may be performed by a known method. In this method, the target molecule (PSA) is immobilized on a solid phase, to which a polynucleotide library comprising polynucleotides having vast kinds of random base sequences is added, and polynucleotides which bind to the target molecule are collected, which polynucleotides are then amplified by PCR, followed by addition of the amplified polynucleotides again to the carrier on which the target molecule is immobilized. By repeating this process about 10 times, aptamers having high binding abilities to the target molecule are concentrated, and the sequences thereof are determined to obtain aptamers recognizing the target molecule.

In the SELEX selection, immobilization of PSA may be carried out simply by physical adsorption such as by air-drying or by covalently bonding PSA to the solid phase by utilizing a carboxyl group or amino group of PSA using a well known-amine coupling agent, or the like. The solid phase to immobilize PSA may be, but not limited to, a nitrocellulose membrane, nylon membrane, filter paper, or the well of a polystyrene microtiter plate, or the like, which adsorbs PSA.

The polynucleotides in the polynucleotide library for SELEX selection have random base sequences of about 30-mer to 100-mer and are synthesized by an automated nucleic acid synthesizer since the sizes of the aptamers are usually about 30-mer to 100-mer. In this case, although the full length of the polynucleotides may be a random base sequence, both end regions of the polynucleotides may also be known base sequences, in order to simplify PCR when SELEX is carried out. In this case, PCR primers can be hybridized to the regions of these known sequences, respectively. The sizes of the regions which are located in both end regions of the polynucleotides are not restricted, and are usually about 10-mer to 25-mer.

Subsequently, the polynucleotide library produced as described above is reacted with the immobilized test substance. The reaction between the library and PSA may preferably be carried out at room temperature. The reaction time is, but not limited to, usually about 1 minute to 30 minutes, and preferably about 10 minutes to 20 minutes. Upon reacting with PSA, aptamers which bind to the PSA are bound to PSA and immobilized on the solid phase. On the other hand, polynucleotides which do not bind to the test substance are not bound to the solid phase and are, therefore, removed by washing.

After removing the polynucleotides which were not bound to the solid phase by washing, the aptamers bound to PSA are eluted. The elution can be carried out, for example, by treating the solid phase with urea at a high concentration of about 6 M to 8 M. Eluted polynucleotides can be collected by a conventional method such as phenol extraction and/or phenol-chloroform extraction and ethanol precipitation. All the collected aptamers are those bound to the immobilized test substance.

Subsequently, PCR is carried out using the collected aptamers as templates, to amplify the aptamers. In cases where polynucleotides which were automatically synthesized have the above described primer binding regions in both end regions, PCR is carried out using those primers. In cases where such primer binding regions are not provided, the polynucleotide sequences of the collected aptamers are determined, and a pair of PCR primers complementary to respective end regions is synthesized, which primers are used for carrying out PCR. By carrying out asymmetric PCR (one of the pair of primers used in PCR is used in an excess amount), mainly single-stranded polynucleotides can be amplified. Alternatively, single-stranded polynucleotides (the strand which is not biotin-labeled) can be collected from the amplified double-stranded polynucleotides by using a biotin-labeled primer as one of the primers used in PCR; binding the amplified double-stranded polynucleotides to avidin beads; denaturing the polynucleotides in this state by NaOH or the like; and collecting the polynucleotides separated from the beads. By this, since only aptamers which bind to the immobilized PSA are amplified, and the numbers of molecules of the aptamers which bind well to the immobilized PSA and which serve as the templates in PCR are large, the percentages thereof in the amplified polynucleotides library become high.

Subsequently, using the library of the amplified aptamers as the polynucleotide library described above, the above series of steps, that is, a cycle of the series of the steps of: reaction with the immobilized test substance; washing; elution and collection of the aptamers; and amplification by PCR; is repeated between about several to ten plus several times. By this, aptamers which bind well to the test substance are concentrated, and aptamers having high binding capacities to the test substance can be obtained.

After SELEX selection, modification of candidate sequences is carried out using a genetic algorithm (GA) in order to obtain modified candidate sequences. In the modification, candidate sequences are allowed to evolve in silico. By application of evolution in silico, it is possible to increase the efficiency of creation of desired aptamers. Modification using GA is described, for example, in Nucleic Acids Research, 2005, 33(12), e108, and Angew. Chem. Int., Ed. 2005, 33, 1061-1065, or the like. In these methods, after finishing the first cycle of the above SELEX, polynucleotide sequences of the obtained aptamers (candidate sequence or pre-SELEX sequence) are determined, the binding capacities thereof to PSA are measured, and the measured binding capacities are sorted in the order of binding capacity. Studies on aptamers to date have demonstrated that the basic structure of an aptamer can be classified into 4 types—that is, the hairpin type, bulge type, pseudoknot type, and guanine quartet type—and which structure is attained by an aptamer having which base sequence, and which is/are the nucleotide(s) necessary for maintenance of the basic structure, can be easily determined by analysis by a computer. In the method utilizing the evolution in silico, crossover, point mutation or a combination thereof are applied. In crossover, a pair of candidate sequences are randomly selected and at least one region of, for example, about 3- to 5-mer, are exchanged with each other among the respective corresponding regions of the respective obtained aptamers. Thereafter, to the above respective regions after crossover, random single base substitutions are introduced. Introduction of these crossover and single base substitutions are carried out in silico. The aptamers having the new polynucleotide sequences created by the computer are chemically synthesized to obtain the second polynucleotide library, which is then used in the above described cycles. When the second polynucleotide library is prepared, aptamers having regions derived from aptamers with high rankings in terms of binding capacity are included in the largest amounts, the ratio thereof being decreased as the ranking becomes lower. Thus, by artificially introducing variations by crossover and random single base substitution in silico, the efficiency of evolution by SELEX can be increased.

The crossover and random single mutation in the modification may preferably be combined to obtain the second polynucleotide library including modified candidate sequences having higher binding ability to PSA. In this case, the modified candidate sequences may be multiple modified candidate sequences obtained by performing either crossover modification or point random mutation modification, selecting first modified candidate sequences from the modified sequences based on PSA binding ability, modifying the first modified candidate sequences by performing whichever of crossover modification or point random mutation modification was not performed when initially obtaining the modified sequences, and selecting based on PSA binding ability from the multiple modified candidate sequences that are first modified candidate sequences that have been modified by performing whichever of crossover modification or point random mutation modification was not performed when initially obtaining the modified sequences.

In order to efficiently obtain an aptamer that binds to PSA with a high binding ability, a method for preparing the aptamer may preferably use some polynucleotide sequence that has a proven history of, when actually used as a pre-SELEX candidate sequence, resulting in manufacture of aptamer having high binding capacity, and may be a method comprising performing at least one modification selected from the group consisting of crossover between sequences and point random mutation of respective sequences, with respect to four preliminary sequences including polynucleotide sequences having SEQ ID Nos. 8 to 11; and selecting, from modified sequences obtained by the at least one modification, a target sequence having higher PSA binding ability than the PSA binding ability of the preliminary sequences. The binding ability of polynucleotide sequences of SEQ ID. No. 8 to 11 are demonstrated as described in the present specification and the binding ability is higher than a polynucleotide obtained by SELEX selection only. Thus, since the sequences obtained from a modification using the polynucleotide sequences of SEQ ID. No. 8 to 11 are then sorted based on the binding ability to PSA of these polynucleotide sequences, an aptamer that binds to PSA can surely be obtained.

TABLE 2

| NAME | SEQUENCE | SEQ. ID NO. |
|------|----------|-------------|
| APSap2#02 | TTTTTAATTAAGGATTTCCCGGTTGTATCTTT | 8 |
| APSap2#18 | TTTTTAATGTCAACGTTGTTTACTGTCCCTTT | 9 |
| APSap2#16 | TTTTTACTGTGAACTCGCCATCAAATATCTTT | 10 |
| APSap2#01 | TTTTTGCCTACTGATTTCCTTTTTGAGCCTTT | 11 |

Alternatively, in order to efficiently obtain an aptamer that binds to PSA with a high binding ability, a method for preparing the aptamer may preferably use other polynucleotide sequence that have a proven history of resulting in manufacture of aptamer having high binding capacity, and be a method comprising performing at least one modification selected from the group consisting of crossover between sequences and point random mutation of respective sequences, with respect to basic sequence comprising a polynucleotide sequence having SEQ ID No. 10; and sorting, from modified sequences obtained by the at least one modification, a target sequence having higher PSA binding ability than the PSA binding ability of a standard sequence having SEQ ID No. 10. Since the binding ability to PSA of the polynucleotide sequence of SEQ ID No. 10 is demonstrated in the present specification to be as high as those of antibodies to PSA, aptamer obtained from sorting using the polynucleotide sequence of SEQ ID: No. 10 may favorably be used as a tool for diagnosis of prostate cancer.

The modification using GA including crossover or point mutation in the method described above may preferably be repeated in order to obtain a target sequence efficiently. The repetition of the modification may simply involve implementation of the steps described above.

The method for diagnosis of prostate cancer of the invention is a method that includes contacting the aptamer described above with a body fluid sample from a subject. According to the method for diagnosis of prostate cancer, since at least one aptamer that binds to PSA with high binding ability is used as a detection tool, the diagnosis is as reliable as diagnoses using antibodies against PSA. Further, since the aptamer of the invention can be produced by automated chemical synthesizers, they can be prepared much more easily and inexpensively than antibodies. Therefore, diagnosis of prostate cancer according to the present invention can be carried out less expensively than by conventional methods.

The method of diagnosis of prostate cancer can be carried out by detection or determination of the PSA as a target substance in the sample. Thus, the method preferably includes contacting the aptamer described above with a body fluid sample from a subject, and detecting the complex of the aptamer and PSA, or determining an amount of the complex of the aptamer and PSA.

The body fluid samples may include, but are not limited to, serum, blood plasma, or dilutions thereof, or the like. The body fluid sample from a subject is allowed to contact the above aptamer. This can be carried out by mixing the sample with an aptamer solution and incubating the resulting mixture. The detection or determination of PSA in the sample may be carried out by an ordinary known method. For example, it is possible that immunoassay such as immunochromatography or ELISA is performed using the aptamer instead of antibodies. Further, a detection method using SPR (surface plasmon resonance) or an aptamer blotting method or the like may be adapted to the diagnosis of the invention. Alternatively, detecting or assaying methods described in WO2005/049826 and WO2007/086403 may be useful using the aptamers of the invention.

The diagnosis of prostate cancer using the aptamer described above may carried out mechanically using an automatic detection device. In the embodiment, a detection device having a sample hold section that holds a detection sample including the body fluid sample from a subject and the aptamer, a detection section that is able to detect a complex of PSA and the aptamer in the detection sample, and a display section that displays a result of the detection from the detection section may be provided. According to the detection device, the diagnosis of prostate cancer may be carried out more easily.

The sample hold section may have any form which can hold the detection sample. Since the detection sample may include a body fluid from the subject and the aptamer that binds to PSA when provided to the detection section, the detection sample may be provided to the sample section as a mixture of the body fluid from the subject and the aptamer, or as separate liquids that include the body fluid or the aptamer and are mixed with each other in the detection device after being provided from the sample hold section.

The detection section has a configuration that can detect binding between PSA and the aptamer, and may be selected in accordance with the specific detection method of the PSA and the aptamer. Examples of the detection method may include, but are not limited to, immunoassay such as immunochromatography, ELISA, or SPR as described above, or the like, and examples of the detection section may include, but are not limited to, a fluorometer, an SPR device, or the like. Further, the detection section has a calculation section that transforms a detection result into detection data. Thus, the result of the detection may be transformed into data.

The display section outputs the detection data produced from the result obtained by the detection section to a display. The display may be any known display used for a such purpose.

By using the detection device, detection of PSA in body fluid from a subject may be performed by automatic detection. In this embodiment, a detection method includes: a step for collecting body fluid from a subject; a step for calculating the amount of PSA in the body fluid sample using aptamer described above to produce detection result data; and a step for outputting the detection result data to the display section. Thus, PSA may be detected easily and a diagnosis for prostate cancer may be carried out based upon the results.

Since the aptamer of the present invention may detect reliably PSA in a body fluid sample from a subject, the aptamer may be used as one component of a kit for PSA detection. In the embodiment, a PSA detection kit comprising; a first container including an aptamer solution comprising the aptamer described above, optional second container including diluent that can be used to dilute the aptamer solution or a body fluid sample from a subject, and a document that explains a procedure of the detection for PSA using the aptamer may be provided. Thus, the detection of PSA may be easily performed.

The configuration of the holding member is not particularly limited as long as it is able to hold the aptamer, and may be selected as appropriate in view of the form of the aptamer included in the kit. For example, when the kit contains the aptamer in solution, the holding member may be a container that can hold a liquid. Further, when the kit contains the aptamer as an immobilized solid phase, the holding member may be a plate or container that can hold an immobilized solid phase.

In addition, the kit may include other aptamer without binding capacity to PSA as a negative control for the PSA detection method.

EXAMPLES

Examples of the present invention will now be described, but the present invention is not limited thereto. "%" in the Examples refers to percentage by weight (mass) unless otherwise specified.

Materials

PSA purified from human semen was purchased from Sigma-Aldrich and Scipac. Synthesized oligonucleotides were purchased from Invitrogen, Greiner Bio-One and Operon Biotechnologies. Nitrocellulose membrane was purchased from GE Healthcare. Human serum was purchased from Nissui. A KAPA2G Fast PCR kit was purchased from KAPA Biosystems. AmpliTaq Gold was purchased from Applied Biosystems. A pGEM vector was purchased from Promega. Avidin—immobilized gel beads were purchased from Pierce. HRP-conjugated anti-FITC antibody was purchased from Dako. Immobilon Western chemiluminescent HRP substrate was purchased from Millipore. PolySorp 96-well polystyrene plate was purchased from Nunc. Blocking reagent N102 was purchased from Nof. BM chemiluminescence ELISA substrate was purchased from Roche. An SA sensor chip was purchased from Biacore. Other reagents were of analytical grade.

Selection of PSA-Binding Aptamer by SELEX

An FITC-labeled single-stranded DNA library containing a 24mer randomized region linked to 20mer primer-binding sequences at both ends through 3mer thymine- ($T_3$-) linker (5'-CATGCTTACCTATAGTGAACTTT($N_{24}$) TTTCTTTGAGAACTGACTCATAC-3': SEQ ID: No. 15) was used. This library was amplified using a forward primer (5'-CATGCTTACCTATAGTGAAC-3': SEQ ID: No. 16) and a reverse primer (5'-GTATGAGTCAGTTCTCAAAG-3% SEQ ID: No. 17). The DNA library was heated at 95° C. for 10 min and then gradually cooled to 25° C. over a period of 30 min in TBS buffer (10 mM Tris/HCl, 150 mM NaCl, 5 mM KCl, 5 mM $MgCl_2$, pH 7.4) to fold structures. PSA (1 μg) was spotted onto a nitrocellulose membrane and air-dried. The PSA-spotted membrane was incubated with 10% (v/v) human serum in the TBS containing 0.5% Tween 20 (TBST) buffer for 1 h to reduce non-specific binding of DNAs to the nitrocellulose membrane. After washing with TBST buffer, the membrane was incubated with the DNA library in TBST buffer for 1 h at room temperature. After washing, the area of the membrane where PSA was spotted was cut out and PSA-bound oligonucleotides were purified by phenol chloroform extraction and ethanol precipitation. The collected oligonucleotides were amplified by PCR using FITC-labeled forward primer, biotin-labeled reverse primer and KAPA2G Fast PCR kit. The single-stranded DNA library for a next cycle of the screening was prepared using avidin-immobilized gel beads. After the $3^{rd}$ round, the selected DNA library was amplified by PCR using AmpliTaq Gold and subcloned into the pGEM vector, and then the sequences of each clone were analyzed.

The PSA-binding abilities of DNA libraries of each round of screening were evaluated by the aptamer blotting method, as previously described (Hasegawa et al. 2008; Yoshida et al. 2009). This will be briefly described in the following section.

Binding Assay of Aptamers to PSA
(1) Aptamer Blotting Assay

The FITC-labeled aptamer was folded as mentioned above. The PSA-spotted membrane was blocked with 4% (v/v) skim milk in TBST buffer and incubated with FITC-labeled aptamer for 1 h at room temperature. After washing, the membrane was incubated with HRP-conjugated anti-FITC antibody for 1 h at room temperature, and then the spot where PSA bound to DNA library was visualized with Immobilon Western chemiluminescent HRP substrate and detected with Typhoon 8600 (GE lifesciences).

(2) Plate Assay

For the use of plate assay, 24mer DNA oligonucleotides were FITC-labeled at their 5'-end through $T_5$-linker and added $T_3$ at their 3'-end resulting in total length of 32mer. 100 µL amounts of PSA in PBS buffer (pH 7.4), at final concentration of 5 µg/mL, were added to a 96-well polystyrene plate. After 2 h incubation with gentle shaking at 37° C., the supernatant was removed and each well was washed with TBST buffer. Each well was filled with 100 µl of five-fold-diluted blocking reagent N102 and incubated with gentle shaking for 1 h at room temperature, and then washed three times. FITC-labeled aptamer was heat treated in TBS buffer as described above for folding. To each well 100 µL amounts of the FITC-labeled aptamer in TBST buffer (5 µM) were added and incubated for 1 h at room temperature. After washing three times, HRP-conjugated anti-FITC antibody was added to each well and incubated with gentle shaking for 1 h at room temperature. Each well was washed five times and BM chemiluminescence HRP substrate was added, then the HRP activity was measured by a multi label plate counter: Wallac 1420 ARVO MX (Perkin Elmer).

Improvement of PSA-Binding Ability Using GA

At the first cycle of sequence control with GA, the oligonucleotide sequences of five aptamers obtained by SELEX were replicated with the same appearance rate in silico and paired randomly with a different sequence to make 10 pairs. The sequences of each pair were crossed over at one random point and two base mutations per sequence were randomly introduced to produce a set of 20 new sequences. The PSA-binding abilities of those 20 sequences were evaluated by plate assay as described above and the sequences were ranked according to their PSA-binding abilities. To produce the next generation, the sequences showing higher PSA-binding ability were selected and replicated with different appearance rates depending on the ranking. After three cycles of GA operation, the oligonucleotide showing the highest PSA-binding ability was found. Then, random one-base mutation was introduced to the oligonucleotide sequence for production of the next generation.

Sensing of PSA by Plate Assay

Plate assay for detection of PSA was performed as described above with the following modifications. One hundred microliter amounts of PSA in PBS buffer (pH 7.4), at various final concentrations of 10 nM to 500 nM, were added to a 96-well polystyrene plate and incubated for 2 h at 37° C. with gentle shaking. After blocking with blocking reagent N 102, 100 µL amounts of 4 µM FITC-labeled ΔPSap4#5 in TBST buffer folded with heat treatment in advance were added to each well and incubated for 1 h at room temperature with gentle shaking. After incubation with HRP-conjugated anti-FITC antibody, chemiluminescence from HRP was measured.

Results
1. Selection of PSA-Binding Aptamer by SELEX

Figure 2:
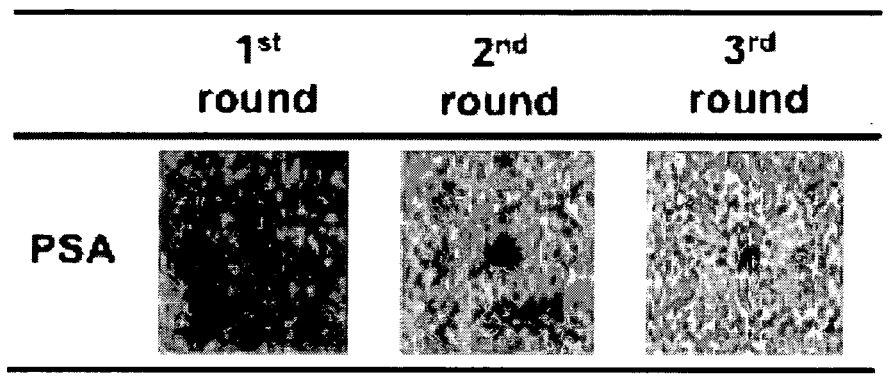
FIG. 2 shows results of binding assay of the DNA library of each round of SELEX to PSA on a nitrocellulose membrane by aptamer blotting.
Figure 3A:
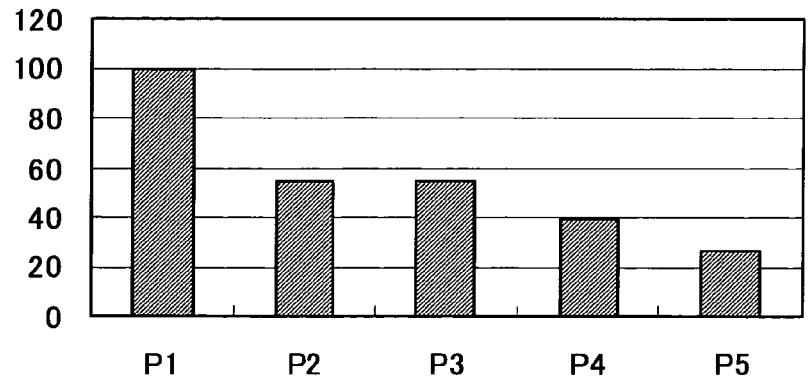
FIG. 3A is a diagram showing the PSA-binding ability of the oligonucleotides in parent generations of GA evolution.
Figure 3B:
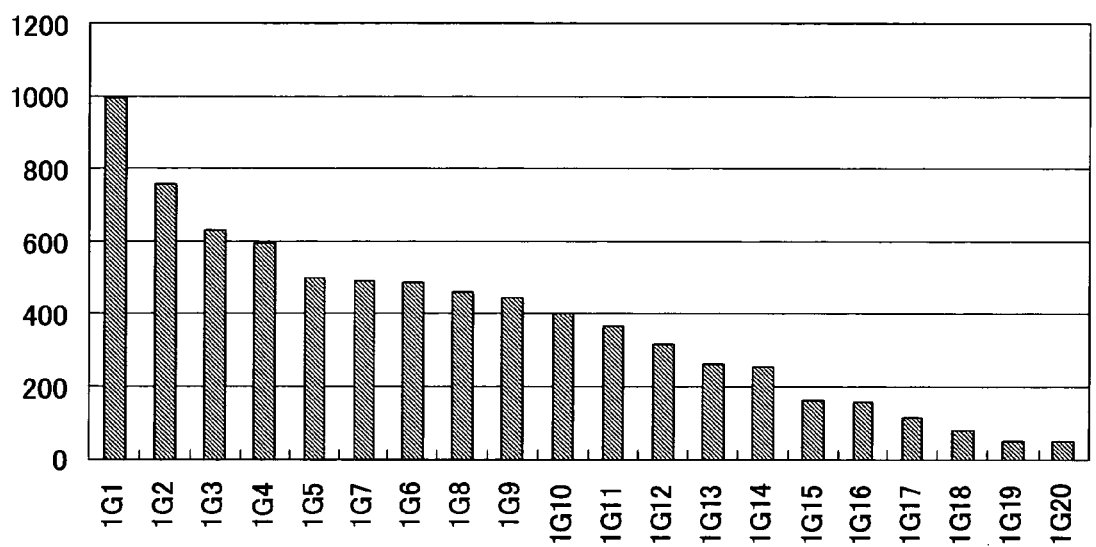
FIG. 3B is a diagram showing the PSA-binding ability of the oligonucleotides in first generations of GA evolution.
Figure 3C:
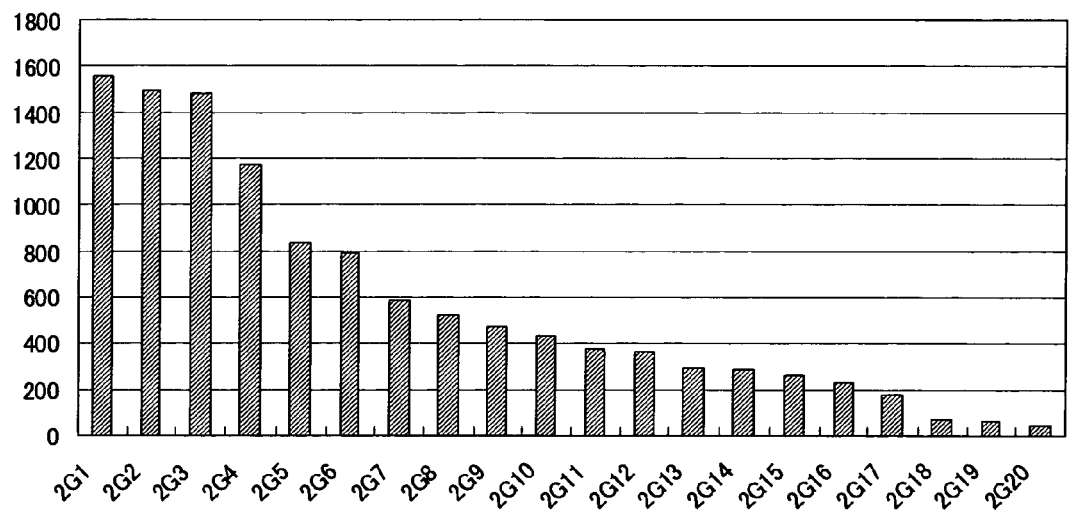
FIG. 3C is a diagram showing the PSA-binding ability of the oligonucleotides in second generations of GA evolution.
Figure 3D:
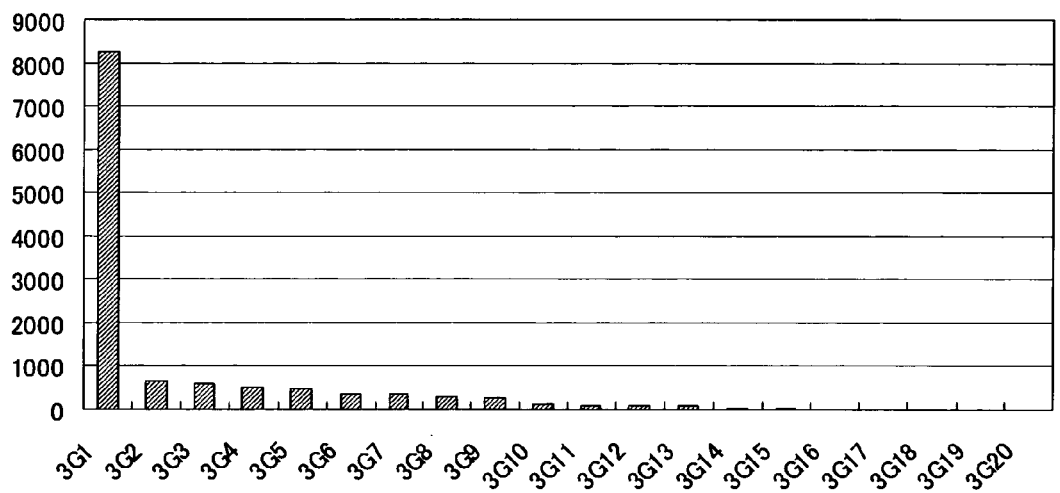
FIG. 3D is a diagram showing the PSA-binding ability of the oligonucleotides in third generations of GA evolution.
Figure 3E:
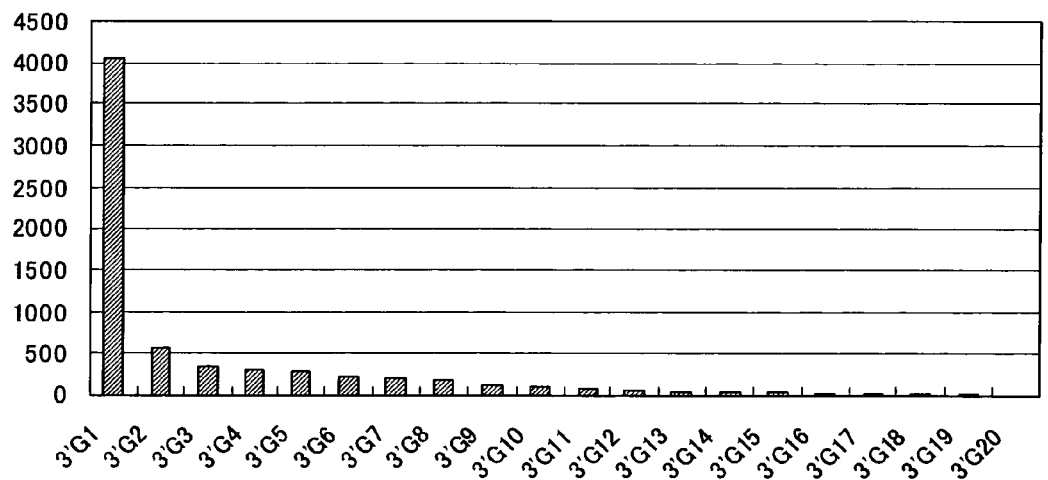
FIG. 3E is a diagram showing the PSA-binding ability of the oligonucleotides in fourth generations of GA evolution.
Figure 3F:
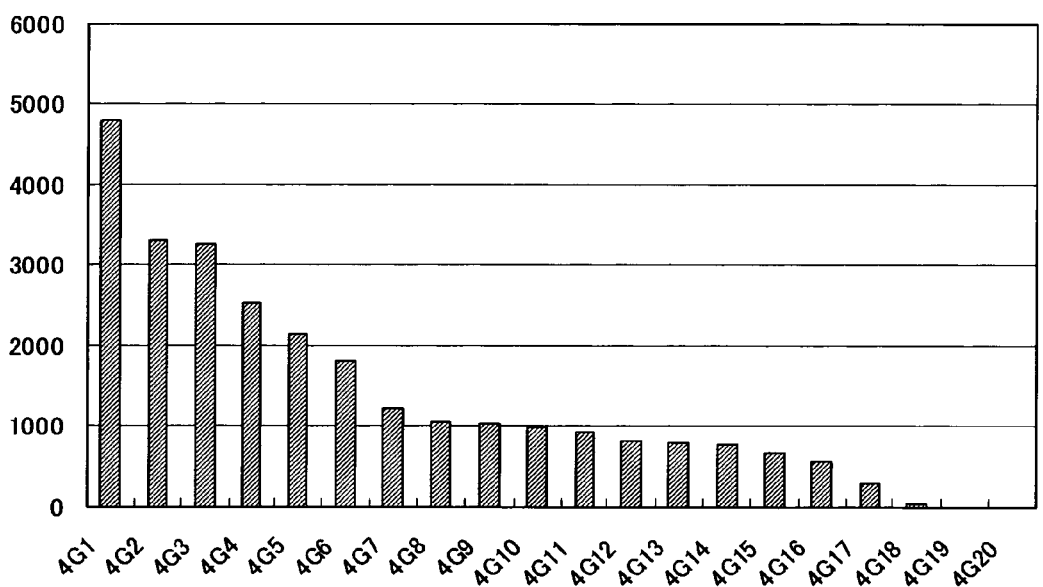
FIG. 3F is a diagram showing the PSA-binding ability of the oligonucleotides in fifth generations of GA evolution.

SELEX was carried out in order to find PSA-binding aptamers as candidates for post-selection using GA. PSA was immobilized on a nitrocellulose membrane and the DNA library which bound to PSA was purified and amplified by PCR using FITC-labeled forward primer and biotin-labeled reverse primer. DNA libraries were incubated with the membrane at a concentration of 1 µM at the first round, 400 nM at the second round and 390 nM at the third round. At the third round of SELEX, a small spot on nitrocellulose membrane representing the binding of the DNA library to PSA was confirmed (FIG. 2). Thus, the oligonucleotide sequences in the DNA library were analyzed. 12 different clones from the third library were sequenced and 11 different sequences were obtained (Table 3). The PSA-binding ability of obtained oligonucleotide sequences was investigated by aptamer blotting method. As a result, five clones named PSap#4-3 (SEQ. ID: No. 20), PSap#4-4 (SEQ. ID: No. 21), PSap#4-6 (SEQ. ID: No. 23), PSap#4-9 (SEQ. ID: No. 25) and PSap#4-11 (SEQ. ID: No. 27), showed binding to PSA on the membrane. In Table 3, the primer binding sites are shown in underlined letters.

TABLE 3

| Name | Occurrence | Sequence | SEQ. ID. No. |
|---|---|---|---|
| PSap#4-1 | 1 | 5'-<u>CATGCTTACCTATAGTGAAC</u>TTGTTATGGATTCACTGCCCAGCGTTT<u>CATGCTTACCTATAGTGAAC</u>-3' | 18 |
| PSap#4-2 | 1 | 5'-<u>CATGCTTACCTATAGTGAAC</u>TTTCCGTCCTTGCCCATCTAGCGTCTTTTT<u>CATGCTTACCTATAGTGAAC</u>-3' | 19 |
| PSap#4-3 | 1 | 5'-<u>CATGCTTACCTATAGTGAAC</u>TTTACTTAATGATTTCCCGGTTGTCTCTTT<u>CATGCTTACCTATAGTGAAC</u>-3' | 20 |
| PSap#4-4 | 2 | 5'-<u>CATGCTTACCTATAGTGAAC</u>TTTCTGGTGTTTATTGTTTACTGTCCCTTT<u>CATGCTTACCTATAGTGAAC</u>-3' | 21 |
| PSap#4-5 | 1 | 5'-<u>CATGCTTACCTATAGTGAAC</u>TTTATTAGCCTCCCGGAAGAGCACCTCTTT<u>CATGCTTACCTATAGTGAAC</u>-3' | 22 |
| PSap#4-6 | 1 | 5'-<u>CATGCTTACCTATAGTGAAC</u>TTTCCGCACCGGGTACGTTTTTGGCCTTT<u>CATGCTTACCTATAGTGAAC</u>-3' | 23 |
| PSap#4-7 | 1 | 5'-<u>CATGCTTACCTATAGTGAAC</u>TTTCTGCGTTCTTTCTTCCTACTTCACGTT<u>CATGCTTACCTATAGTGAAC</u>-3' | 24 |
| PSap#4-9 | 1 | 5'-<u>CATGCTTACCTATAGTGAAC</u>TTTAATATCAACTTGCCATCAAATATCTTT<u>CATGCTTACCTATAGTGAAC</u>-3' | 25 |
| PSap#4-10 | 1 | 5'-<u>CATGCTTACCTATAGTGAAC</u>TTTTGGCGCAGTACTGGTCTACCTGGCTTT<u>CATGCTTACCTATAGTGAAC</u>-3' | 26 |
| PSap#4-11 | 1 | 5'-<u>CATGCTTACCTATAGTGAAC</u>TTTGTGTTGCCCGGAACGTCGTGGCCCTTT<u>CATGCTTACCTATAGTGAAC</u>-3' | 27 |
| PSap#4-12 | 1 | 5'-<u>CATGCTTACCTATAGTGAAC</u>TTTCCGTTGTAGCCTGGCTTCTACCTATTT<u>CATGCTTACCTATAGTGAAC</u>-3' | 28 |

Improvement of PSA-Binding Ability Using GA

While an aptamer with high PSA-binding ability is required for the use thereof as a recognition element in PSA sensing, SELEX may fail to screen a high affinity aptamer because of the limitation of sequence diversity in the library and the PCR bias described above.

In order to carry out a post-SELEX screening of aptamers using GA with candidates, the five sequences pre-selected through SELEX were used as "parents" to produce a set of 20 oligonucleotide sequences using GA. These oligonucleotides were synthesized and the PSA-binding ability was evaluated by plate assay. The PSA-binding ability was measured by detection chemiluminescence from HRP-conjugated anti-FITC antibody that represented the binding of oligonucleotides against PSA immobilized on a well of polystyrene plate (n=2). The signal intensity was normalized with that of the top oligonucleotide in the 1st-generation. Then, the oligonucleotides were ranked according to PSA-binding ability, and top four ranked sequences were chosen to produce a next set of oligonucleotide sequences. The cycle of oligonucleotide synthesis, plate assay and evolution of the oligonucleotide sequences using GA was repeated three times, with one cycle corresponding to one generation when we assume this process to be the in silico evolution of the PSA-binding aptamer. After one cycle of GA operations, four 2nd-generation sequences, SEQ ID: Nos. 8 to 11, were obtained. After a total of three cycles of GA operations, random one-base mutation was introduced at the sequence that showed the highest PSA-binding ability of the 3rd-generation in order to produce the 4th-generation. The number of top ranked sequences selected to produce a next generation and the appearance rate of oligonucleotide sequences to replicate for pairing were varied in each generation (Table 4).

PSA-binding ability of the aptamers using GA. The 1st-generation oligonucleotides showed up to 10-fold higher PSA-binding ability than that of the parent oligonucleotides obtained by SELEX. After ranking of those oligonucleotides, the top-seven oligonucleotide sequences were selected for the production of the 2nd-generation. Those top-seven sequences were replicated in silico with a different appearance rate of 5:4:3:2:2:2:2:2 depending on the PSA-binding ability, crossed over with a paired different sequence and then added with two-base mutation per one sequence randomly. The 2nd-generation oligonucleotides showed PSA-binding ability up to 1.6-fold higher than that of the 1st-generation oligonucleotides and 16-fold higher than the parent oligonucleotides obtained by SELEX.

Moreover, top-four oligonucleotide sequences, SEQ ID. Nos. 8 to 11, were selected from the 2nd-generation for production of the 3rd-generation. The appearance rate for replication of those top-four sequences was fixed at 6:5:5:4 to produce the 3rd-generation. The replicated sequences were crossed over with a randomly paired different sequence. Then, random one-base mutation was introduced into each sequence to produce a set of 20 oligonucleotide sequences as the 3rd-generation. As a result, one sequence named ΔPSap3'#4 (SEQ ID: No. 2) in the 3rd-generation was obtained using ΔPSap2#2 (SEQ. ID. No. 8), ΔPSap2#18 (SEQ. ID. No. 9), ΔPSap2#16 (SEQ. ID. No. 10) and ΔPSap2#1 (SEQ. ID. No. 11). The sequence named ΔPSap3'#4 showed higher PSA-binding ability than that of the 2nd-generation oligonucleotides. It showed significantly high PSA-binding ability and it was 40-fold higher than the parent oligonucleotides obtained by SELEX. Therefore, a set of 20 different oligonucleotide sequences as the 4th-generation were produced by introducing random one-base mutation at the sequence of ΔPSap3'#4 without any crossover. In

TABLE 4

| Generation | Ranking | Name | Sequence | Appearance rate | SEQ. ID. No. |
|---|---|---|---|---|---|
| Parent | 1 | ΔPSap#4-3 | TTTTTACTTAATGATTTCCCGGTTGTCTCTTT | 4 | 29 |
| | 2 | ΔPSap#4-4 | TTTTTCTGGTGTTTATTGTTTACTGTCCCTTT | 4 | 30 |
| | 3 | ΔPSap#4-11 | TTTTTGTGTTGCCCGGAACGTCGTGGCCCTTT | 4 | 31 |
| | 4 | ΔPSap#4-9 | TTTTTAATATCAACTTGCCATCAAATATCTTT | 4 | 32 |
| | 5 | ΔPSap#4-6 | TTTTTCCGCACCGGGTACGTTTTTTGGCCTTT | 4 | 33 |
| 1st generation | 1 | ΔPSap1#13 | TTTTTAATATCAACTTGCCATAAAGGGCCTTT | 5 | 34 |
| | 2 | ΔPSap1#3 | TTTTTACTTAAGGATTTCCTTTTTTAGCCTTT | 4 | 35 |
| | 3 | ΔPSap1#16 | TTTTTAATGTCAACTCGCCATCAAATATCTTT | 3 | 36 |
| | 4 | ΔPSap1#5 | TTTTTCCTCACCGGGTAACTTCGTGGCCCTTT | 2 | 37 |
| | 5 | ΔPSap1#12 | TTTTTAATATCACCCTTGTTTACTGTCCCTTT | 2 | 38 |
| | 6 | ΔPSap1#15 | TTTTTGCCTAATGATTTCCCGGTTGTCTCTTT | 2 | 39 |
| | 7 | ΔPSap1#19 | TTTTTACTTAATGATTTCACCGGTGGCCCTTT | 2 | 40 |
| 2nd generation | 1 | ΔPSap2#2 | TTTTTAATTAAGGATTTCCCGGTTGTATCTTT | 6 | 8 |
| | 2 | ΔPSap2#18 | TTTTTAATGTCAACGTTGTTTACTGTCCCTTT | 5 | 9 |
| | 3 | ΔPSap2#16 | TTTTTACTGTGAACTCGCCATCAAATATCTTT | 5 | 10 |
| | 4 | ΔPSap2#1 | TTTTTGCCTACTGATTTCCTTTTTGAGCCTTT | 4 | 11 |
| 3rd generation | 1 | ΔPSap3'#4 | TTTTTAATTAAGGCTCGCCATCAAATAGCTTT | 20 | 2 |

The PSA-binding ability of each oligonucleotide in each generation is shown in Table 5 and FIG. 3. The PSA-binding ability of oligonucleotides was improved as cycles of GA operations continued. This indicated the improvement of the fourth-generation, ΔPSap4#5 (TTTTTAAT-TAAAGCTCGCCATCAAATAGCTTT: SEQ ID: No. 1) showed the highest PSA-binding ability and it was 48-fold higher than the parent oligonucleotides. See, Table 5.

TABLE 5

| | Name | Normalized HRP chemiluminescence (CPS) | Sequence | SEQ. ID: No. |
|---|---|---|---|---|
| 1 | ΔPSap4#5 | 4804 | TTTTTAATTAAAGCTCGCCATCAAATAGCTTT | 1 |
| 2 | ΔPSap3'#04 | 4060 | TTTTTAATTAAGGCTCGCCATCAAATAGCTTT | 2 |
| 3 | ΔPSap4#10 | 3305 | TTTTTTATTAAGGCTCGCCATCAAATAGCTTT | 3 |
| 4 | ΔpSap4#7 | 3258 | TTTTTAATTAAGGCTCGCCATCAGATAGCTTT | 4 |
| 5 | ΔPSap4#14 | 2514 | TTTTTAATTAAGGCTCGCCATCAAAGAGCTTT | 5 |
| 6 | ΔPSap4#11 | 2152 | TTTTTAATTAAGGCTCGCCATCAAATAACTTT | 6 |
| 7 | ΔPSap4#1 | 1803 | TTTTTAATTCAGGCTCGCCATCAAATAGCTTT | 7 |
| 8 | ΔPSap2#02 | 1554 | TTTTTAATTAAGGATTTCCCGGTTGTATCTTT | 8 |
| 9 | ΔPSap2#18 | 1487 | TTTTTAATGTCAACGTTGTTTACTGTCCCTTT | 9 |
| 10 | ΔpSap2#16 | 1478 | TTTTTACTGTGAACTCGCCATCAAATATCTTT | 10 |
| 11 | ΔPSap4#19 | 1221 | TTTTTAATTAAGGCTCGCCATCAAAAAGCTTT | 41 |
| 12 | ΔPSap2#01 | 1172 | TTTTTGCCTACTGATTTCCTTTTTGAGCCTTT | 11 |

Sensing of PSA by Plate Assay

Figure 4:
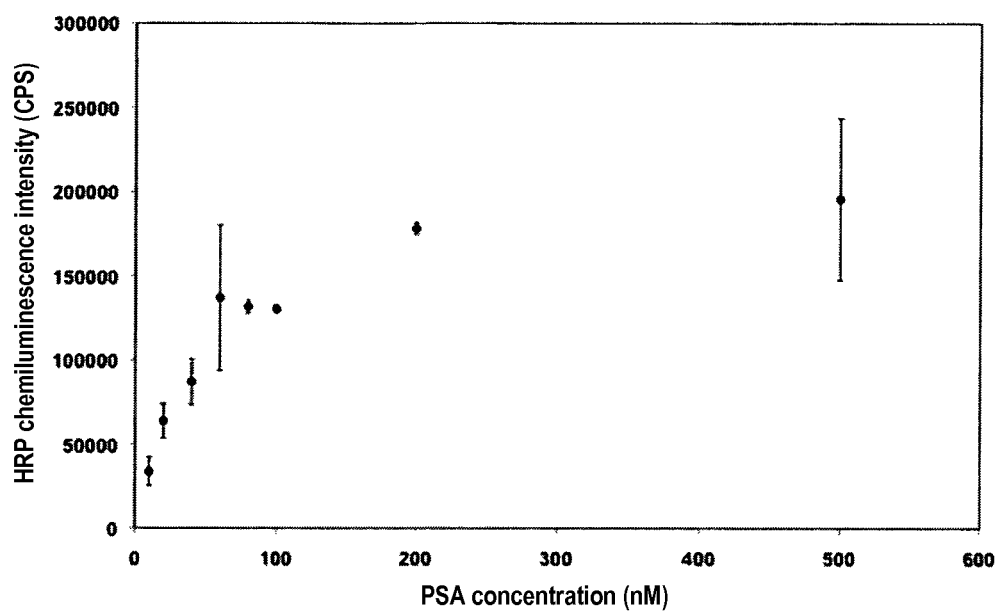
FIG. 4 is a diagram showing a result of sensing of PSA by plate assay using ΔPSap4#5 selected through GA operations.

Plate assay was performed to measure PSA concentrations with ΔPSap4#5 selected using GA as the top oligonucleotide of the 4th-generation. In the assay, various concentrations of PSA in PBS buffer were added to each well of a polystyrene plate to immobilize PSA. Then, the PSA concentration was measured by detecting chemiluminescence from HRP-conjugated anti-FITC antibody that represented the binding of FITC-labeled ΔPSap4#5 against PSA immobilized on a well of polystyrene plate (n=2). As a result, an HRP chemiluminescence signal representing the binding of ΔPSap4#5 to PSA was yielded depending on PSA concentration immobilized to polystyrene plate at concentrations of 0.3 µg/mL to 6 µg/mL, which correspond to 10 nM to 200 nM (FIG. 4). The binding dissociation constant (Ku) for the interaction of ΔPSap4#5 with PSA was estimated to be 54 nM. This value of $K_D$ is the almost same as those of antibodies that bind to PSA.

The $K_D$ value of general antibodies is said to be from $1 \times 10^{-6}$ to $1 \times 10^{-8}$. From the results of testing binding using HRP, the measured values of HRP shown in Table 5 in excess of 1000 CPS from ΔPSap4#5 to ΔPSap2#16 clearly exhibit the same binding capacity as antibodies.

Further, ΔPSap4#5 has the highest binding capacity. It seems that, by comparing the structure of ΔPSap4#5 (Tm: 57.2° C., ΔG=−4.74 kcal/mol) and ΔPSap3'19004 (Tm: 39.6° C., ΔG=−1.63 kcal/mol), the binding ability of the aptamer may be improved by introducing one point mutation at the first stem region, but not limited to the position.

According to the present invention, aptamers that bind to PSA are provided. A diagnosis method for prostate cancer may be carried out reliably and easily using the aptamers.

All the documents, patent applications and technical standards described in the present specification are hereby incorporated by reference to the same extent as in cases where each document, patent application or technical standard is specifically and individually described as being incorporated by reference.

The invention claimed is:

1. An aptamer comprising:
a preceding region having a random polynucleotide sequence consisting of from 1 to 10 nucleotides;
a first region, at a 3' end of the preceding region, consisting of nnnnCT wherein each n is independently selected from A, T, G and C;
a second region consisting of nnCTTT wherein each n is independently selected from A, T, G and C, and at least one part of the second region is complementary to the first region; and
a third region positioned between the first region and the second region and consisting of a random polynucleotide sequence having from 3 to 30 nucleotides,
wherein the aptamer is capable of binding to prostate-specific antigen (PSA).

2. The aptamer according to claim 1, wherein the first region is (A or C)A(A or G)GCT.

3. The aptamer according to claim 1, wherein the second region is (A or C)(A or G)CTTT.

4. The aptamer according to claim 1, wherein the third region consist of CGCCATCAGAT (SEQ ID NO: 13) or a polynucleotide sequence having from 1 to 5 bases that are different therefrom.

5. The aptamer according to claim 1, wherein the preceding region consists of $T_m$(A or T)(A or C)T(T or G), and m is an integer of 1 to 10.

6. The aptamer according to claim 1, wherein the preceding region consists of TTTTTAATT or TTTTTAATG, or a polynucleotide sequence having 1 or 2 bases that are different from either of these sequences.

7. The aptamer according to claim 1, wherein the aptamer is any one of:
(1) polynucleotides of SEQ ID Nos. 1 to 7,
(2) polynucleotides having the same sequence as SEQ ID Nos. 1 to 7, except that from one to 5 nucleotides are different in each of the third region and the preceding region, respectively, or
(3) polynucleotides having the same sequence as SEQ ID Nos. 1 to 7, except that a total of from one to 5 nucleotides are different in the first region and the second region thereof, and from one to 5 nucleotides are different in each of the third region and the preceding region, respectively.

8. A method for forming a complex comprising PSA, comprising contacting the aptamer according to claim 1 with a body fluid sample from a subject.

9. The method according to claim 8, further comprising detecting the complex of the aptamer and PSA.

10. The method according to claim 8, further comprising determining an amount of the complex of the aptamer and PSA.

* * * * *

SEQUENCE LISTING

<160> NUMBER OF SEQ ID NOS: 41

<210> SEQ ID NO 1
<211> LENGTH: 32
<212> TYPE: DNA
<213> ORGANISM: Artificial
<220> FEATURE:
<223> OTHER INFORMATION: d_PSap4#5

<400> SEQUENCE: 1
tttttaatta aagctcgcca tcaaatagct tt          32

<210> SEQ ID NO 2
<211> LENGTH: 32
<212> TYPE: DNA
<213> ORGANISM: Artificial
<220> FEATURE:
<223> OTHER INFORMATION: d_PSap3'#04

<400> SEQUENCE: 2
tttttaatta aggctcgcca tcaaatagct tt                 32

<210> SEQ ID NO 3
<211> LENGTH: 32
<212> TYPE: DNA
<213> ORGANISM: Artificial
<220> FEATURE:
<223> OTHER INFORMATION: d_PSap4#10

<400> SEQUENCE: 3
tttttaatta aggctcgcca tcaaatagct tt                 32

<210> SEQ ID NO 4
<211> LENGTH: 32
<212> TYPE: DNA
<213> ORGANISM: Artificial
<220> FEATURE:
<223> OTHER INFORMATION: d_PSap4#7

<400> SEQUENCE: 4
tttttaatta aggctcgcca tcagatagct tt                 32

<210> SEQ ID NO 5
<211> LENGTH: 32
<212> TYPE: DNA
<213> ORGANISM: Artificial
<220> FEATURE:
<223> OTHER INFORMATION: d_PSap4#14

<400> SEQUENCE: 5
tttttaatta aggctcgcca tcaaagagct tt                 32

<210> SEQ ID NO 6
<211> LENGTH: 32
<212> TYPE: DNA
<213> ORGANISM: Artificial
<220> FEATURE:
<223> OTHER INFORMATION: d_PSap4#11

<400> SEQUENCE: 6
tttttaatta aggctcgcca tcaaataact tt                 32

<210> SEQ ID NO 7
<211> LENGTH: 32
<212> TYPE: DNA
<213> ORGANISM: Artificial
<220> FEATURE:
<223> OTHER INFORMATION: d_PSap4#1

<400> SEQUENCE: 7
tttttaattc aggctcgcca tcaaatagct tt                 32

<210> SEQ ID NO 8
<211> LENGTH: 32
<212> TYPE: DNA
<213> ORGANISM: Artificial
<220> FEATURE:
<223> OTHER INFORMATION: d_PSap2#02

<400> SEQUENCE: 8
tttttaatta aggatttccc ggttgtatct tt                 32

```
<210> SEQ ID NO 9
<211> LENGTH: 32
<212> TYPE: DNA
<213> ORGANISM: Artificial
<220> FEATURE:
<223> OTHER INFORMATION: d_PSap2#18

<400> SEQUENCE: 9
tttttaatgt caacgttgtt tactgtccct tt                                    32

<210> SEQ ID NO 10
<211> LENGTH: 32
<212> TYPE: DNA
<213> ORGANISM: Artificial
<220> FEATURE:
<223> OTHER INFORMATION: d_PSap2#16

<400> SEQUENCE: 10
tttttactgt gaactcgcca tcaaatatct tt                                    32

<210> SEQ ID NO 11
<211> LENGTH: 32
<212> TYPE: DNA
<213> ORGANISM: Artificial
<220> FEATURE:
<223> OTHER INFORMATION: d_PSa[@0002]#01

<400> SEQUENCE: 11
tttttgccta ctgatttcct ttttgagcct tt                                    32

<210> SEQ ID NO 12
<211> LENGTH: 11
<212> TYPE: DNA
<213> ORGANISM: Artificial
<220> FEATURE:
<223> OTHER INFORMATION: 3rt region 1

<400> SEQUENCE: 12
cgccatcaaa t                                                           11

<210> SEQ ID NO 13
<211> LENGTH: 11
<212> TYPE: DNA
<213> ORGANISM: Artificial
<220> FEATURE:
<223> OTHER INFORMATION: 3rd region 2

<400> SEQUENCE: 13
cgccatcaga t                                                           11

<210> SEQ ID NO 14
<211> LENGTH: 11
<212> TYPE: DNA
<213> ORGANISM: Artificial
<220> FEATURE:
<223> OTHER INFORMATION: 3rd region 3

<400> SEQUENCE: 14
cgccatcaaa g                                                           11

<210> SEQ ID NO 15
<211> LENGTH: 70
<212> TYPE: DNA
<213> ORGANISM: Artificial
<220> FEATURE:
<223> OTHER INFORMATION: Initiation sequence
```

```
<220> FEATURE:
<221> NAME/KEY: misc_feature
<222> LOCATION: (24)..(47)
<223> OTHER INFORMATION: n is a, c, g, or t

<400> SEQUENCE: 15
catgcttacc tatagtgaac tttnnnnnnn nnnnnnnnnn nnnnnnnttt ctttgagaac    60
tgactcatac                                                          70

<210> SEQ ID NO 16
<211> LENGTH: 20
<212> TYPE: DNA
<213> ORGANISM: Artificial
<220> FEATURE:
<223> OTHER INFORMATION: primer_F

<400> SEQUENCE: 16
catgcttacc tatagtgaac                                               20

<210> SEQ ID NO 17
<211> LENGTH: 20
<212> TYPE: DNA
<213> ORGANISM: Artificial
<220> FEATURE:
<223> OTHER INFORMATION: prime_R

<400> SEQUENCE: 17
gtatgagtca gttctcaaag                                               20

<210> SEQ ID NO 18
<211> LENGTH: 67
<212> TYPE: DNA
<213> ORGANISM: Artificial
<220> FEATURE:
<223> OTHER INFORMATION: PSas#4-1

<400> SEQUENCE: 18
catgcttacc tatagtgaac ttgttatgga ttcactgccc agcgtttcat gcttacctat    60
agtgaac                                                             67

<210> SEQ ID NO 19
<211> LENGTH: 70
<212> TYPE: DNA
<213> ORGANISM: Artificial
<220> FEATURE:
<223> OTHER INFORMATION: PSap#4-2

<400> SEQUENCE: 19
catgcttacc tatagtgaac tttccgtcct tgcccatcta gcgtctttttt catgcttacc   60 tatagtgaac                                                          70

<210> SEQ ID NO 20
<211> LENGTH: 70
<212> TYPE: DNA
<213> ORGANISM: Artificial
<220> FEATURE:
<223> OTHER INFORMATION: PSap#4-3

<400> SEQUENCE: 20
catgcttacc tatagtgaac tttacttaat gatttcccgg ttgtctcttt catgcttacc    60
tatagtgaac                                                          70
```

```
<210> SEQ ID NO 21
<211> LENGTH: 70
<212> TYPE: DNA
<213> ORGANISM: Artificial
<220> FEATURE:
<223> OTHER INFORMATION: PSap#4-4

<400> SEQUENCE: 21
catgcttacc tatagtgaac tttctggtgt ttattgttta ctgtccctttt catgcttacc    60 tatagtgaac                                                           70

<210> SEQ ID NO 22
<211> LENGTH: 70
<212> TYPE: DNA
<213> ORGANISM: Artificial
<220> FEATURE:
<223> OTHER INFORMATION: PSap#4-5

<400> SEQUENCE: 22
catgcttacc tatagtgaac tttattagcc tcccggaaga gcacctcttt catgcttacc    60
tatagtgaac                                                           70

<210> SEQ ID NO 23
<211> LENGTH: 70
<212> TYPE: DNA
<213> ORGANISM: Artificial
<220> FEATURE:
<223> OTHER INFORMATION: PSap#4-6

<400> SEQUENCE: 23
catgcttacc tatagtgaac tttccgcacc gggtacgttt tttggccttt catgcttacc    60
tatagtgaac                                                           70

<210> SEQ ID NO 24
<211> LENGTH: 70
<212> TYPE: DNA
<213> ORGANISM: Artificial
<220> FEATURE:
<223> OTHER INFORMATION: PSap#4-7

<400> SEQUENCE: 24
catgcttacc tatagtgaac tttctgcgtt ctttcttcct acttcacgtt catgcttacc    60
tatagtgaac                                                           70

<210> SEQ ID NO 25
<211> LENGTH: 70
<212> TYPE: DNA
<213> ORGANISM: Artificial
<220> FEATURE:
<223> OTHER INFORMATION: PSap#4-9

<400> SEQUENCE: 25
catgcttacc tatagtgaac tttaatatca acttgccatc aaatatcttt catgcttacc    60
tatagtgaac                                                           70

<210> SEQ ID NO 26
<211> LENGTH: 70
<212> TYPE: DNA
<213> ORGANISM: Artificial
<220> FEATURE:
<223> OTHER INFORMATION: PSap#4-10
```

```
<400> SEQUENCE: 26
catgcttacc tatagtgaac ttttggcgca gtactggtct acctggcttt catgcttacc        60
tatagtgaac                                                               70

<210> SEQ ID NO 27
<211> LENGTH: 70
<212> TYPE: DNA
<213> ORGANISM: Artificial
<220> FEATURE:
<223> OTHER INFORMATION: PSap#4-11

<400> SEQUENCE: 27
catgcttacc tatagtgaac tttgtgttgc ccggaacgtc gtggcccttt catgcttacc        60
tatagtgaac                                                               70

<210> SEQ ID NO 28
<211> LENGTH: 70
<212> TYPE: DNA
<213> ORGANISM: Artificial
<220> FEATURE:
<223> OTHER INFORMATION: PSap#4-12

<400> SEQUENCE: 28
catgcttacc tatagtgaac tttccgttgt agcctggctt ctacctattt catgcttacc        60
tatagtgaac                                                               70

<210> SEQ ID NO 29
<211> LENGTH: 32
<212> TYPE: DNA
<213> ORGANISM: Artificial
<220> FEATURE:
<223> OTHER INFORMATION: d_PSap#4-3

<400> SEQUENCE: 29
tttttactta atgatttccc ggttgtctct tt                                      32

<210> SEQ ID NO 30
<211> LENGTH: 32
<212> TYPE: DNA
<213> ORGANISM: Artificial
<220> FEATURE:
<223> OTHER INFORMATION: d_PSap#4-4

<400> SEQUENCE: 30
tttttctggt gtttattgtt tactgtccct tt                                      32

<210> SEQ ID NO 31
<211> LENGTH: 32
<212> TYPE: DNA
<213> ORGANISM: Artificial
<220> FEATURE:
<223> OTHER INFORMATION: d-PSap#4-11

<400> SEQUENCE: 31
tttttgtgtt gcccggaacg tcgtggccct tt                                      32

<210> SEQ ID NO 32
<211> LENGTH: 32
<212> TYPE: DNA
<213> ORGANISM: Artificial
<220> FEATURE:
<223> OTHER INFORMATION: d-PSap#4-9
```

```
<400> SEQUENCE: 32
tttttaatat caacttgcca tcaaatatct tt                              32

<210> SEQ ID NO 33
<211> LENGTH: 32
<212> TYPE: DNA
<213> ORGANISM: Artificial
<220> FEATURE:
<223> OTHER INFORMATION: d-PSap#4-6

<400> SEQUENCE: 33
tttttccgca ccgggtacgt tttttggcct tt                              32

<210> SEQ ID NO 34
<211> LENGTH: 32
<212> TYPE: DNA
<213> ORGANISM: Artificial
<220> FEATURE:
<223> OTHER INFORMATION: d-PSap1#13

<400> SEQUENCE: 34
tttttaatat caacttgcca taaagggcct tt                              32

<210> SEQ ID NO 35
<211> LENGTH: 32
<212> TYPE: DNA
<213> ORGANISM: Artificial
<220> FEATURE:
<223> OTHER INFORMATION: d-PSap1#3

<400> SEQUENCE: 35
tttttactta aggatttcct tttttagcct tt                              32

<210> SEQ ID NO 36
<211> LENGTH: 32
<212> TYPE: DNA
<213> ORGANISM: Artificial
<220> FEATURE:
<223> OTHER INFORMATION: d-PSap1#16

<400> SEQUENCE: 36
tttttaatgt caactcgcca tcaaatatct tt                              32

<210> SEQ ID NO 37
<211> LENGTH: 32
<212> TYPE: DNA
<213> ORGANISM: Artificial
<220> FEATURE:
<223> OTHER INFORMATION: d-PSap1#5

<400> SEQUENCE: 37
tttttcctca ccgggtaact tcgtggccct tt                              32

<210> SEQ ID NO 38
<211> LENGTH: 32
<212> TYPE: DNA
<213> ORGANISM: Artificial
<220> FEATURE:
<223> OTHER INFORMATION: d-PSap1#12

<400> SEQUENCE: 38
tttttaatat caccttgtt tactgtccct tt                               32
```

```
<210> SEQ ID NO 39
<211> LENGTH: 32
<212> TYPE: DNA
<213> ORGANISM: Artificial
<220> FEATURE:
<223> OTHER INFORMATION: d-PSap1#15

<400> SEQUENCE: 39
tttttgccta atgatttccc ggttgtctct tt                                 32

<210> SEQ ID NO 40
<211> LENGTH: 32
<212> TYPE: DNA
<213> ORGANISM: Artificial
<220> FEATURE:
<223> OTHER INFORMATION: d-PSap1#19

<400> SEQUENCE: 40
tttttactta atgatttcac cggtggccct tt                                 32

<210> SEQ ID NO 41
<211> LENGTH: 32
<212> TYPE: DNA
<213> ORGANISM: Artificial
<220> FEATURE:
<223> OTHER INFORMATION: d-PSap4#19

<400> SEQUENCE: 41
tttttaatta aggctcgcca tcaaaaagct tt                                 32
```